United States Patent

Penn et al.

[11] Patent Number: 5,906,640
[45] Date of Patent: May 25, 1999

[54] BIFURCATED STENT AND METHOD FOR THE MANUFACTURE AND DELIVERY OF SAME

[75] Inventors: Ian M. Penn; Donald R. Ricci, both of Vancouver, Canada; George A. Shukov, Los Altos, Calif.

[73] Assignee: Divysio Solutions ULC, Canada

[21] Appl. No.: 08/850,742

[22] Filed: May 2, 1997

Related U.S. Application Data

[63] Continuation-in-part of application No. 08/605,189, Feb. 28, 1996, Pat. No. 5,755,771.

[30] Foreign Application Priority Data

Mar. 11, 1997 [CA] Canada ................................. 2134997

[51] Int. Cl.⁶ .......................................................... A61F 2/06
[52] U.S. Cl. ........................................................... 623/1
[58] Field of Search ............................................ 623/1, 12

[56] References Cited

U.S. PATENT DOCUMENTS

| | | | |
|---|---|---|---|
| 5,639,278 | 6/1997 | Dereume | 623/1 |
| 5,643,340 | 7/1997 | Nunokawa | 623/1 |
| 5,653,743 | 8/1997 | Martin | 623/1 |
| 5,676,696 | 10/1997 | Marcade | 623/1 |
| 5,676,697 | 10/1997 | McDonald | 623/1 |
| 5,693,086 | 12/1997 | Goicoechea | 63/1 |
| 5,709,713 | 1/1998 | Evans | 623/1 |

*Primary Examiner*—Michael J. Milano
*Attorney, Agent, or Firm*—Fitzpatrick, Cella, Harper & Scinto

[57] ABSTRACT

An expandable bifurcated stent comprising a proximal end and a distal end in communication with one another. The proximal end comprises a primary passageway and the distal end comprises a pair of secondary passageways. The stent is expandable from a first, contracted position to a second, expanded position upon the application of a radially outward force exerted on the stent. Each of the primary passageway and the secondary passageway being constructed of has a porous surface. A method for production of a bifurcated stent is also described. Preferably, the method comprises the step of connecting a first stent section to a second stent section, the first stent section having an end thereof adapted for connection to an opening disposed along the length of a second stent section.

46 Claims, 11 Drawing Sheets

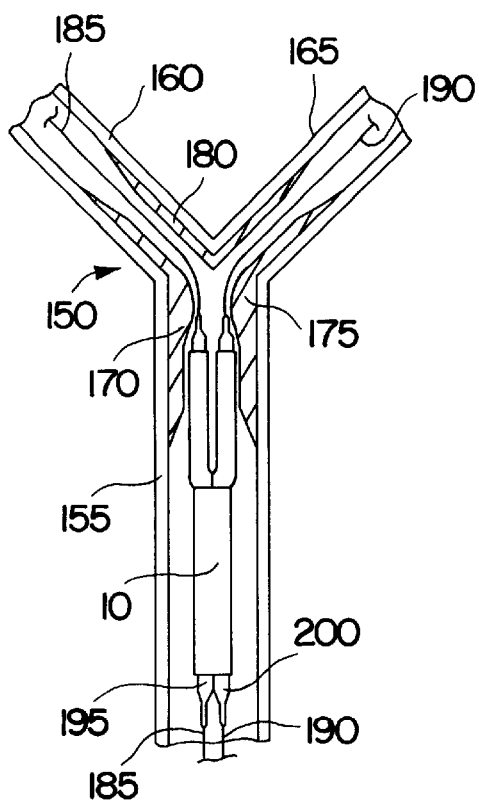
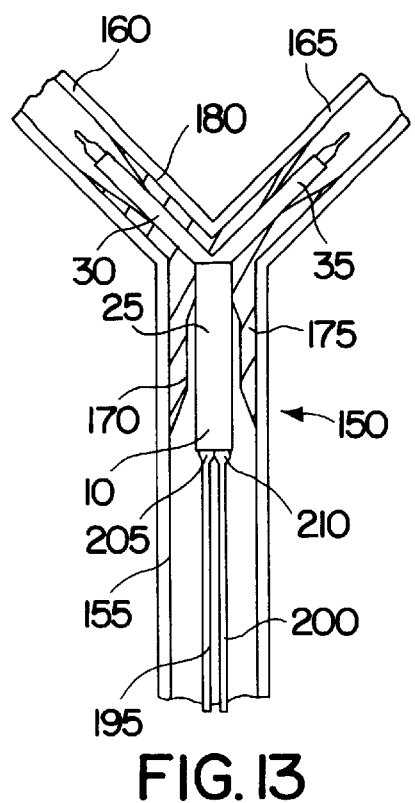
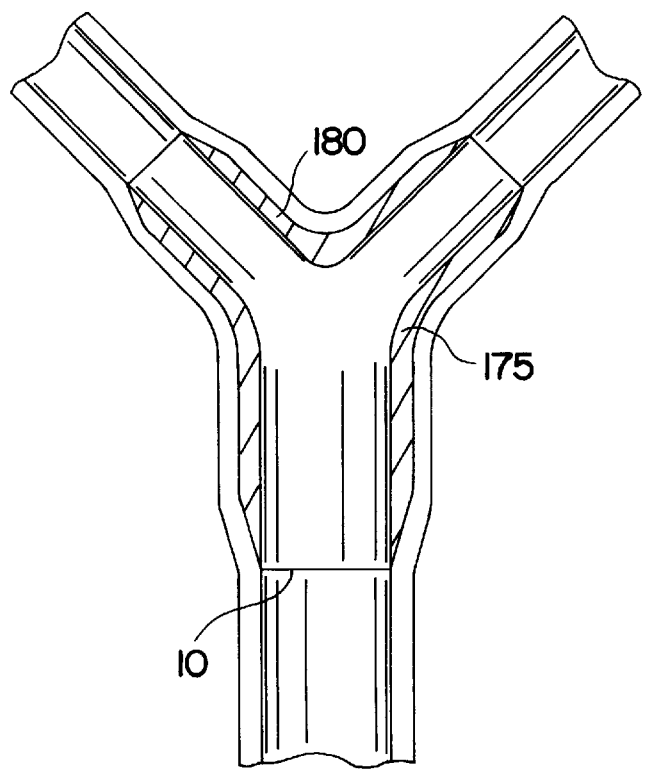
FIG. 12
FIG. 13
FIG. 14

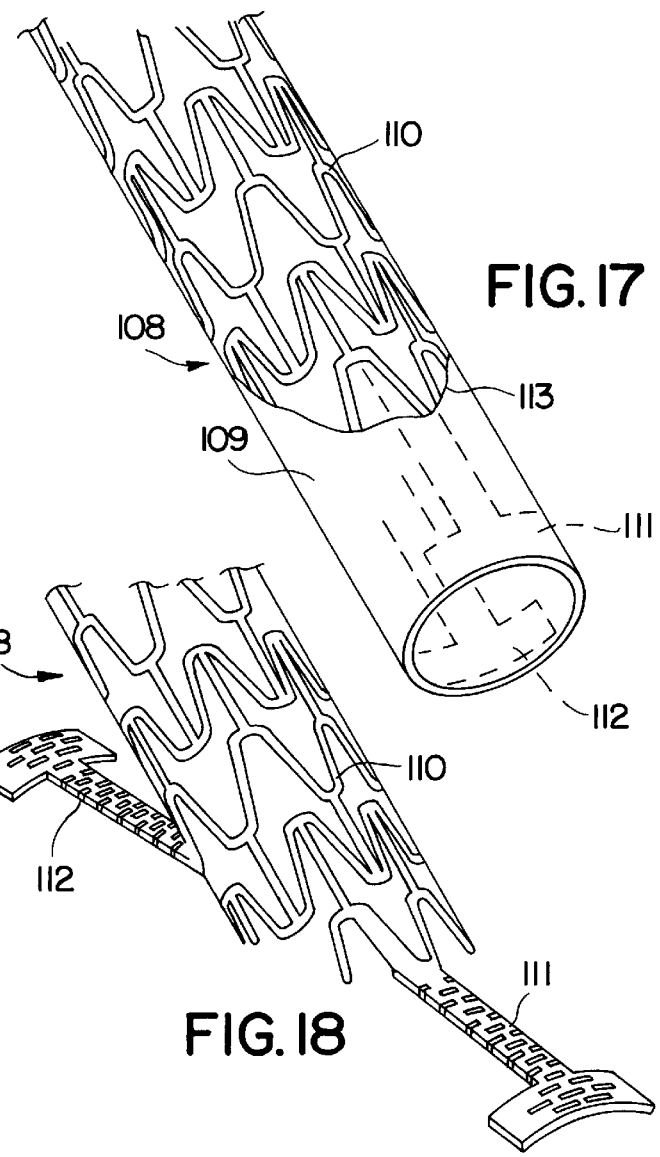
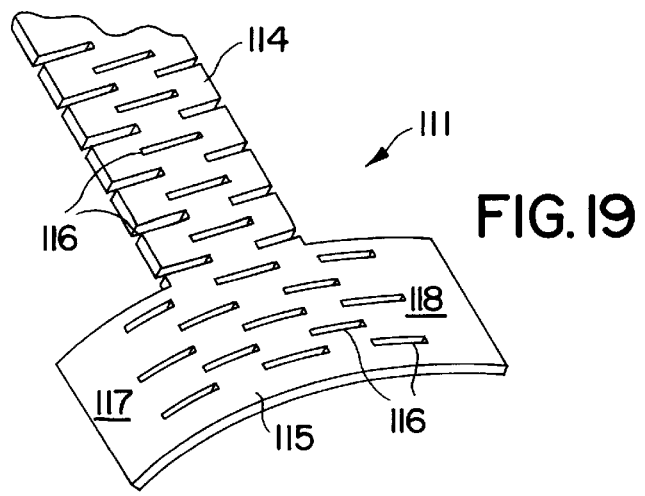

BIFURCATED STENT AND METHOD FOR THE MANUFACTURE AND DELIVERY OF SAME

This application is a continuation-in-part of U.S. patent application Ser. No. 08/605,189, filed Feb. 28, 1996, now U.S. Pat. No. 5,755,771, issued May 26, 1998.

BACKGROUND OF THE INVENTION

1. Field of the Invention

The present invention relates to a bifurcated stent and to a method for the manufacture and delivery of a bifurcated stent.

2. Description of the Prior Art

Stents are generally known. Indeed, the term "stent" has been used interchangeably with terms such as "intraluminal vascular graft" and "expansible prosthesis". As used throughout this specification the term "stent" is intended to have a broad meaning and encompasses any expandable prosthetic device for implantation in a body passageway (e.g., a lumen or artery).

In the past six to eight years, the use of stents has attracted an increasing amount of attention due the potential of these devices to be used, in certain cases, as an alternative to surgery. Generally, a stent is used to obtain and maintain the patency of the body passageway while maintaining the integrity of the passageway. As used in this specification, the term "body passageway" is intended to have a broad meaning and encompasses any duct (e.g., natural or iatrogenic) within the human body and can include a member selected from the group comprising: blood vessels, respiratory ducts, gastrointestinal ducts and the like.

Initial stents were self-expanding, spring-like devices which were inserted in the body passageway in a contracted state. When released, the stent would automatically expand and increase to a final diameter dependent on the size of the stent and the elasticity of the body passageway. Such stents are known in the art as the Wallstent™.

The self-expanding stents were found by some investigators to be deficient since, when deployed, they could place undue, permanent stress on the walls of the body passageway. This lead to the development of various stents which were controllably expandable at the target body passageway so that only sufficient force to maintain the patency of the body passageway was applied in expanding the stent.

Generally, in these later systems, a stent, in association with a balloon, is delivered to the target area of the body passageway by a catheter system. Once the stent has been properly located (the target area of the body passageway can be filled with a contrast medium to facilitate visualization during fluoroscopy), the balloon is expanded thereby expanding the stent, e.g. by plastic deformation of the stent structure, so that the latter is urged in place against the body passageway. As indicated above, the amount of force applied is at least that necessary to maintain the patency of the body passageway. At this point, the balloon is deflated and withdrawn within the catheter, and subsequently removed. Ideally, the stent will remain in place and maintain the target area of the body passageway substantially free of blockage (or narrowing).

A stent which has gained some notoriety in the art is known as the Palmaz-Schatz™ Balloon Expandable Stent (hereinafter referred to as "the Palmaz-Schatz stent"). This stent is discussed in a number of patents including U.S. Pat. Nos. 4,733,665, 4,739,762, 5,102,417 and 5,316,023, the contents of each of which are hereby incorporated by reference.

Another stent which has gained some notoriety in the art is known as Gianturco-Roubin Flex-Stent™ (hereinafter referred to as "the Gianturco-Roubin stent"). This stent is discussed in a number of patents including U.S. Pat. Nos. 4,800,882, 4,907,336 and 5,041,126, the contents of each of which are hereby incorporated by reference.

Other types of stents are disclosed in the following patents:

U.S. Pat. No. 5,035,706 (Gianturco et al.),
U.S. Pat. No. 5,037,392 (Hillstead),
U.S. Pat. No. 5,147,385 (Beck et al.),
U.S. Pat. No. 5,282,824 (Gianturco),
Canadian patent 1,239,755 (Wallsten), and
Canadian patent 1,245,527 (Gianturco et al.), the contents of each of which are hereby incorporated by reference.

All of the stents described in the above-identified patents share the common design of being mono-tubular and thus, are best suited to be delivered and implanted in-line in the body passageway. These known stents are inappropriate for use in a bifurcated body passageway (e.g. a body passageway comprising a parent passageway that splits into a pair of passageways). Further, these stents are inappropriate for use in a body passageway having side branches since: (i) accurate placement of the stent substantially increases the risk to the patient, (ii) the risk of passageway closure in the side branches is increased, and (iii) the side branches will be substantially inaccessible.

Indeed the Physician Guide published in support of the Palmaz-Schatz stent states on page 32 (the contents of which are hereby incorporated by reference):

". . . no attempt should be made following placement of a PALMAZ-SCHATZ stent to access the side branch with a guide wire or a balloon, as such attempts may result in additional damage to the target vessel or the stent. Attempts to treat obstructed side branches within stented segments can result in balloon entrapment, necessitating emergency bypass surgery."

Thus, when installed, the Palmaz-Schatz stent admittedly shields side branches emanating from the target area of the body passageway effectively permanently. This can be problematic since the only way to treat blockage or other problems associated with the side branches is to perform the type of surgery which installation of the stent was intended to avoid.

This contraindication for conventional mono-tubular stents is corroborated by a number of investigators. See, for example, the following:

1. *Interventional Cardiovascular Medicine: Principles and Practice* (1994); Publisher: Churchill Livingstone Inc.; pages 221–223 (Ohman et al.), 487–488 (Labinaz et al.), 667–668 (Bashore et al.) and 897 (Bailey et al.), including references cited therein;
2. Gianturco-Roubin Flex-Stent™ Coronary Stent: Physician's Guide; page 2, Paragraph 3 under WARNINGS;
3. *Circulation*, Vol. 83, No. 1, January 1991 (Schatz et al.); entitled "Clinical Experience With the Palmaz-Schatz Coronary Stent"; pages 148–161 at page 149; and
4. *American Heart Journal*, Vol. 127, No. 2, February 1994 (Eeckhout et al.); entitled "Complications and follow-up after intracoronary stenting: Critical analysis of a 6-year single-center experience"; pages 262–272 at page 263, the contents of each of which are hereby incorporated by reference.

Further, some investigators have attempted to install individual stents in each branch of the bifurcated body passageway. However, this approach is fraught with at least two significant problems. First, implantation of three individual stents, together with the expansive forces generated upon implantation results in subjecting the central walls of the bifurcated body passageway to undue stress which may lead to post-procedural complications. Second, since the central walls of the bifurcated body passageway are not supported by the individual stents, this area of the passageway is left substantially unprotected and susceptible to blockage.

One particular problem area with bifurcated body passageways is the occurrence of bifurcation lesions within the coronary circulation. Generally, these legions may be classified as follows:

| Type | Characteristic |
| --- | --- |
| A | Prebranch stenosis not involving the ostium of the side branch; |
| B | Postbranch stenosis of the parent vessel not involving the origin of the side branch; |
| C | Stenosis encompassing the side branch but not involving the ostium; |
| D | Stenosis involving the parent vessel and ostium of the side branch; |
| E | Stenosis involving the ostium of the side branch only; and |
| F | Stenosis discretly involving the parent vessel and ostium of the side branch. |

See *Atlas of Interventional Cardiology* (Popma et al.), 1994, pages 77–79, the contents of which are hereby incorporated by reference. The presence of bifurcation lesions is predictive of increased procedural complications including acute vessel closure.

Detailed classification of other bifurcated body passageways is relatively undeveloped given the lack of non-surgical treatment approaches.

U.S. Pat. No. 4,994,071 (MacGregor) discloses a bifurcating stent apparatus. The particular design incorporates a series of generally parallel oriented loops interconnected by a sequence of "half-birch" connections. The lattice structure of the illustrated stent is constructed of wire. The use of such wire is important to obtain the loop structure of the illustrated design. The use of a wire loop construction is disadvantageous since it is complicated to manufacture and the resulting stent is subject to expansion variability (e.g. variable post-expansion distortion and the like).

U.S. Pat. Nos. 3,993,078 (Bergentz et al.) and 5,342,387 (Summers) also disclose and illustrate a bifurcated stent design constructed of wire. These designs suffer from the same disadvantages as the design described in the previous paragraph.

It would be desirable to have a reliable, expandable bifurcated stent since this would be useful in treating aneurysms, blockages and other ailments. It would be further desirable to have a practical method for producing such a stent. It would also be desirable if such a stent was relatively easy to install.

SUMMARY OF THE INVENTION

It is an object of the present invention to provide a novel expandable bifurcated stent which obviates or mitigates at least one of the above-mentioned disadvantages of the prior art.

It is another object of the present invention to provide a novel method for the manufacture of an expandable bifurcated stent.

It is another object of the present invention to provide a novel method for implanting an expandable bifurcated stent.

Accordingly, in one of its aspects, the present invention provides an expandable bifurcated stent comprising a proximal end and a distal end in communication with one another, the proximal end comprising a primary passageway and the distal end comprising a pair of secondary passageways, each secondary passageway in communication with the primary passageway at a first intersection, the stent being expandable from a first, contracted position to a second, expanded position upon the application of a radially outward force exerted on the stent, each of the primary passageway and the secondary passageways, being constructed of a tubular wall having a porous surface, at least one connection portion being disposed at the first intersection for reinforcing the first intersection.

In another of its aspects, the present invention provides expandable bifurcated stent comprising a proximal end and a distal end in communication with one another, the proximal end comprising a primary passageway and the distal end comprising a pair of secondary passageways, each secondary passageway in communication with the primary passageway at a first intersection, the stent being expandable from a first, contracted position to a second, expanded position upon the application of a radially outward force exerted on the stent, each of the primary passageway and the secondary passageways having a porous surface, at least one connection portion interconnecting the pair of secondary passageways for reinforcing the first intersection.

In yet another of its aspects, the present invention provides a method for production of a bifurcated stent comprising the step of connecting a first stent section to a second stent section, the first stent section having an end thereof adapted for connection to an opening disposed along the length of a second stent section.

In yet another of its aspects, the present invention provides a method for production of a bifurcated stent comprising the steps of:

(i) connecting a first stent section to a second stent section to provide a connection portion;

(ii) provide an opening in the connection portion;

(iii) connecting a third stent section to the connection portion.

In yet another of its aspects, the present invention provides a method for production of a bifurcated stent comprising the steps of:

passing a first stent section having a first opening disposed along a length thereof through a second stent section having a second opening disposed along a length thereof, the first stent section having a diameter less than a diameter of the second stent section;

passing a leading end of the first stent section through the second opening of the second stent section; and substantially aligning the first opening and the second opening with respect to one another.

In yet another of its aspects, the present invention provides a method for delivery to a target body passageway of an expandable bifurcated stent comprising a proximal end and a distal end in communication with one another, the proximal end comprising a primary passageway and the distal end comprising a pair of secondary passageways, the stent being expandable from a first, contracted position to a second, expanded position upon the application of a radially outward force exerted on the stent, each of the primary passageway and the secondary passageway being constructed of a tubular wall having a porous surface, the method comprising the steps of:

disposing the stent in the first, contracted position on a catheter;

inserting the stent and catheter within the target body passageway by catheterization of the target body passageway;

exerting a radially outward expansive force on the stent such that the stent assumes the second, expanded position and is urged against the target body passageway.

Thus, an aspect of the present invention relates to the provision of an expandable bifurcated stent constructed of a tubular wall having a porous surface. As used throughout this specification, the term "tubular wall", when used in relation to a stent, is intended to mean a substantially cylindrical tube which subsequently has been subjected to an etching (e.g. by laser, chemical or other suitable means) or similar technique to remove pre-selected portions of the cylindrical tube thereby providing a porous surface on the tube—this is distinct from a stent constructed of wire bent to a selected shape/design. To the knowledge of the Applicant's, an expandable bifurcated stent having such a tubular wall has heretofore been unknown.

As used throughout this specification, the term "bifurcated stent" is intended to have a broad meaning and encompasses any stent having a primary passageway to which is connected at least two secondary passageways. Thus, trifurcated stents are encompassed herein. Further, one of the secondary passageways can be a continuation of the primary passageway with the result that the other secondary passageway is essentially a side branch to the primary passageway.

The Applicant's have also discovered that various repeating patterns in the porous surface of the tubular wall are particularly advantageous. Generally, the repeating pattern is a polygon having a pair of side walls substantially parallel to the longitudinal axis of the stent passageway in question, a first concave-shaped wall and a second convex-shaped wall connecting the side walls. The various repeating patterns which are useful in the context of the present invention are disclosed in the following copending patent applications filed in the name of the assignee of the present invention:

Canadian patent application number 2,134,997 (filed Nov. 3, 1994);

Canadian patent application number 2,171,047 (filed Mar. 5, 1996);

Canadian patent application number 2,175,722 (filed May 3, 1996);

Canadian patent application number 2,185,740 (filed Sep. 17, 1996);

International patent application PCT/CA97/00151 (filed Mar. 5, 1997); and

International patent application PCT/CA97/00152 (filed Mar. 5, 1997);

the contents of each of which are hereby incorporated by reference (hereinafter collectively referred to as the "Divysio patent applications").

The present bifurcated stent may be constructed from any suitable starting material. Preferably, the starting material is a thin tube of a metal or alloy (non-limiting examples include stainless steel, titanium, tantalum, nitinol, Elgiloy, NP35N and mixtures thereof) which would then have sections thereof cut or etched out to leave a repeating pattern, inter alia, such as one or more of those disclosed in the Divysio patent applications.

The stent of the present invention may further comprise a coating material thereon. The coating material may be disposed continuously or discontinuously on the surface of the stent. Further, the coating may be disposed on the interior and/or the exterior surface(s) of the stent. The coating material may be one or more of a biologically inert material (e.g. to reduce the thrombogenicity of the stent), a medicinal composition which leaches into the wall of the body passageway after implantation (e.g. to provide anticoagulant action, to deliver a pharmaceutical to the body passageway and the like) and the like.

The stent is preferably provided with a biocompatible coating, in order to minimize adverse interaction with the walls of the body vessel and/or with the liquid, usually blood, flowing through the vessel. The coating is preferably a polymeric material, which is generally provided by applying to the stent a solution or dispersion of preformed polymer in a solvent and removing the solvent. Non-polymeric coating material may alternatively be used. Suitable coating materials, for instance polymers, may be polytetraflouroethylene or silicone rubbers, or polyurethanes which are known to be biocompatible. Preferably, however, the polymer has zwitterionic pendant groups, generally ammonium phosphate ester groups, for instance phosphoryl choline groups or analogues thereof. Examples of suitable polymers are described in published International patent applications WO-A-93/16479 and WO-A-93/15775. Polymers described in those specifications are hemo-compatible as well as generally biocompatible and, in addition, are lubricious. When a biocompatible coating is used, it is important to ensure that the surfaces of the stent are completely coated in order to minimize unfavourable interactions, for instance with blood, which might lead to thrombosis.

This good coating can be achieved by suitable selection of coating conditions, such as coating solution viscosity, coating technique and/or solvent removal step.

BRIEF DESCRIPTION OF THE DRAWINGS

Embodiments of the present invention will be described with reference to the accompanying drawings wherein like numerals designate like parts and in which:

FIG. 12 illustrates a cross-section of a bifurcated body passageway into which the a bifurcated stent produced according to the present method of manufacture is being delivered;

FIG. 13 illustrates a cross-section of a bifurcated body passageway in which the bifurcated stent is positioned in a first, contracted position;

FIG. 14 illustrates a cross-section of a bifurcated body passageway in which the bifurcated stent is positioned in a second, expanded position;

FIGS. 17–22 illustrate various preferred features of the bifurcated stent illustrated in FIGS. 15 and 16.

DETAILED DESCRIPTION OF THE PREFERRED EMBODIMENTS

Figure 1:
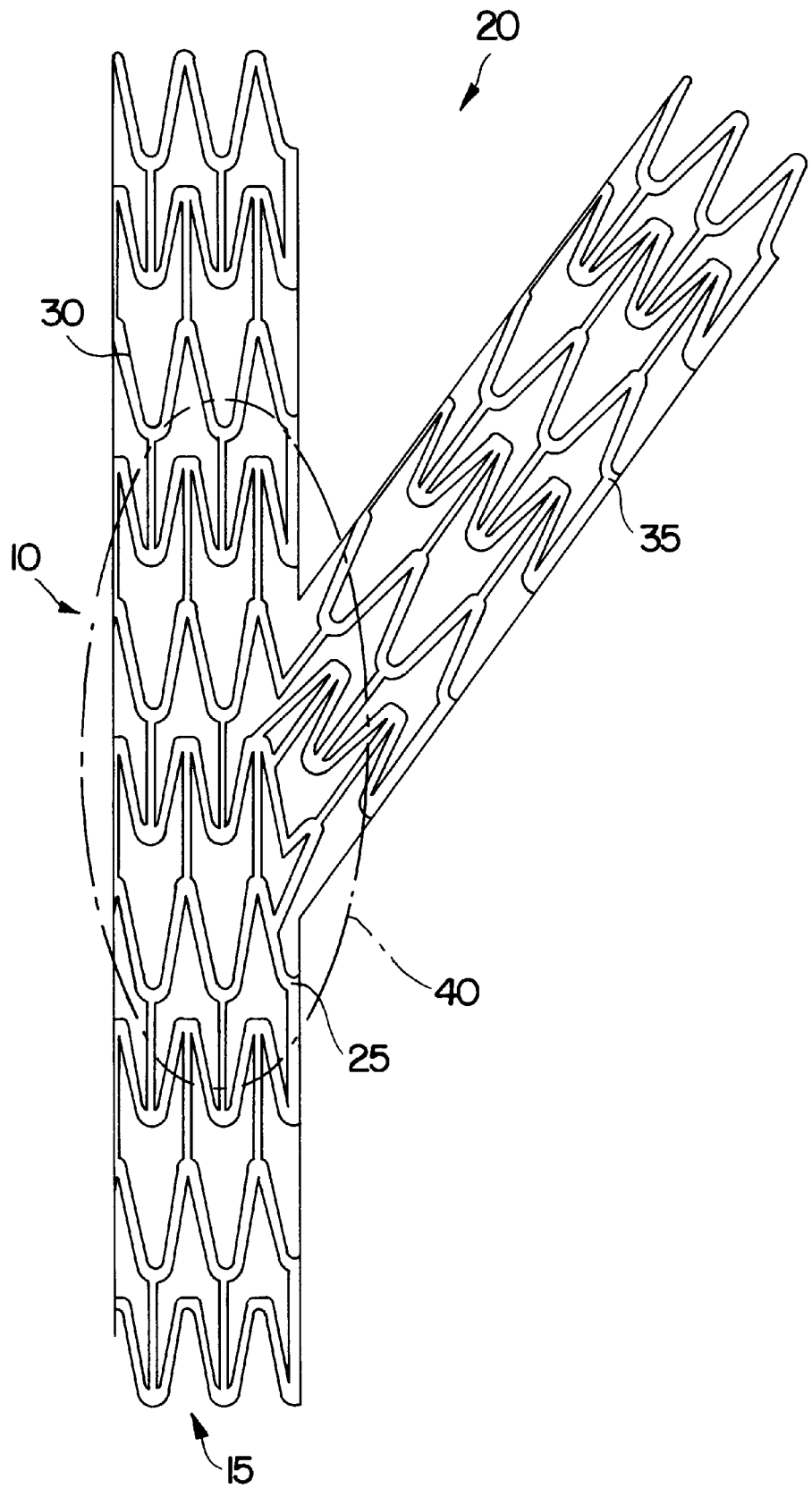
FIG. 1 illustrates a side elevation of a bifurcated stent in accordance with the present invention.

With reference to FIG. 1, there is illustrated a stent 10. Stent 10 comprises a proximal end 15 and a distal end 20. Proximal end 15 comprises a primary passageway 25. Distal end 20 comprises a pair of secondary passageways 30,35. Secondary passageways 30,35 are connected to primary passageway 25 at an intersection point 40.

As will be apparent to those of skill in the art, stent 10 incorporates the porous surface design illustrated in copending Canadian patent application number 2,134,944, referred to above. As discussed above, this design may be varied to incorporate other designs such as those disclosed in the other Divysio patent applications.

Figure 2:
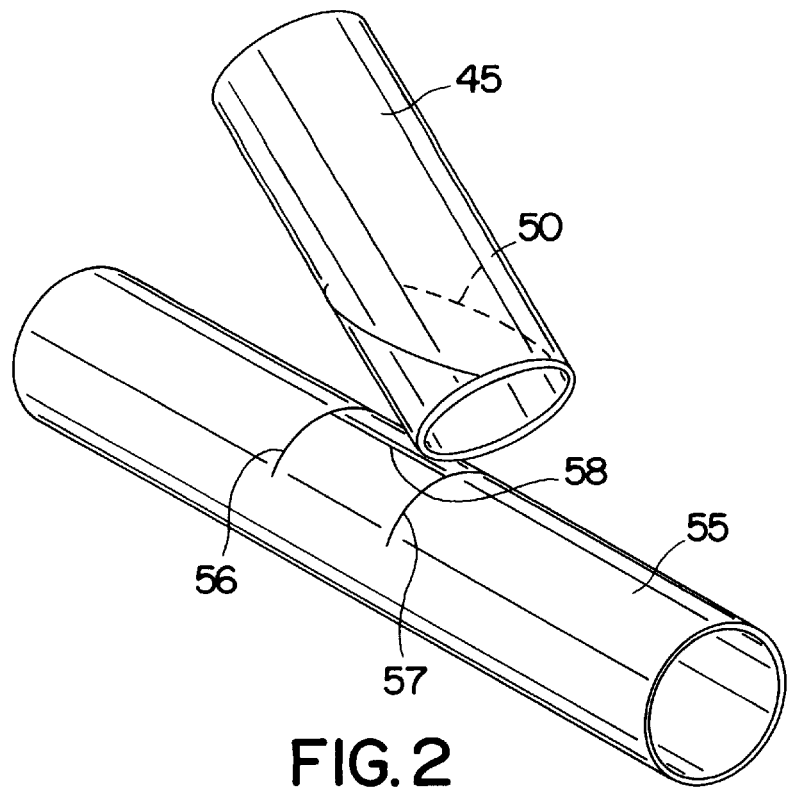
FIGS. 2–4 illustrate a first embodiment of a method for production of a bifurcated stent.
Figure 3:
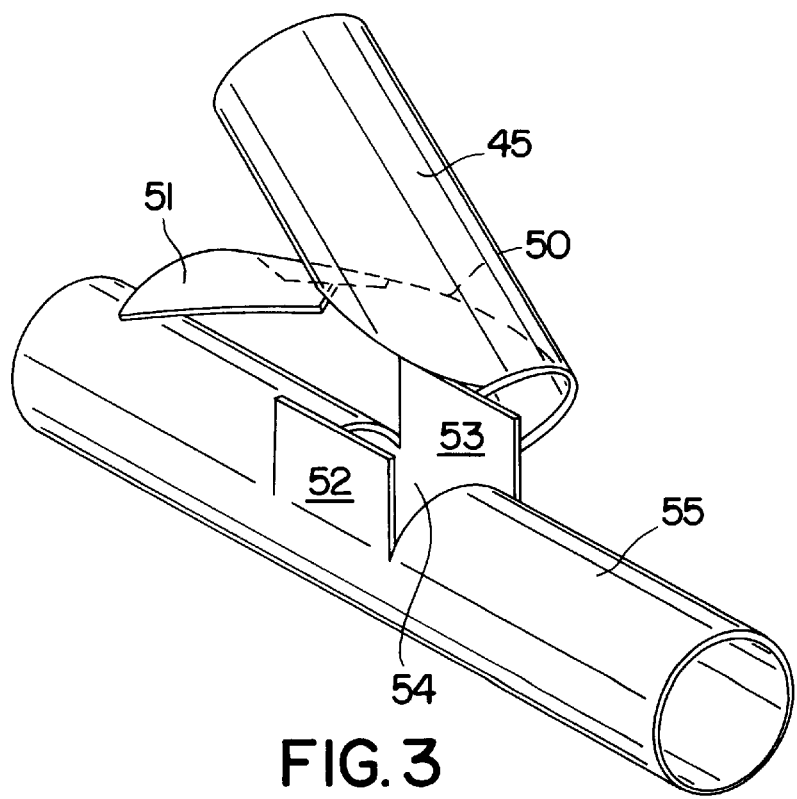
Figure 4:
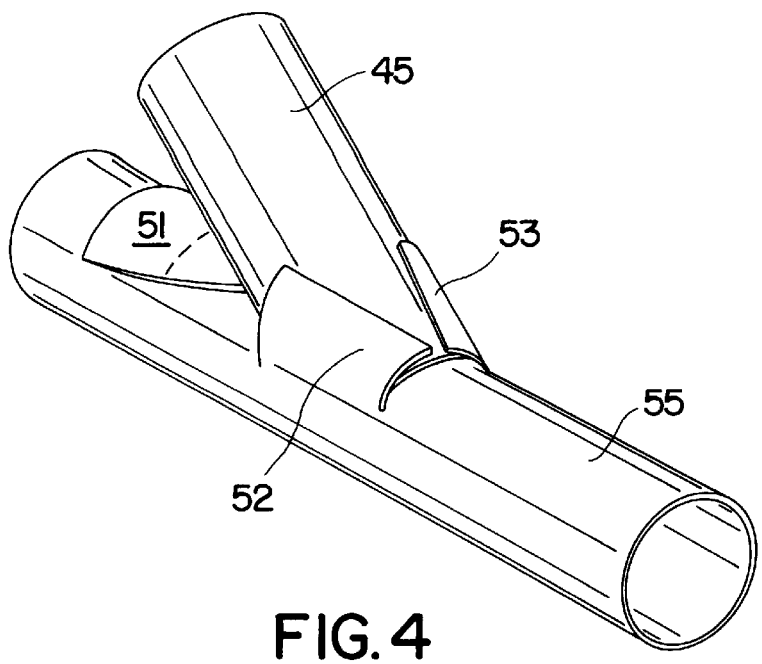

With reference to FIGS. 2–4, an embodiment of the present method for production of a bifurcated stent is illustrated. For ease of illustration, the porous surface of the tubular wall of the stent is not illustrated.

As illustrated, a first stent section 45 comprises a cylindrical tube having a bevelled cut 50 made adjacent one end of the cylindrical tube. Those of skill in the art will recognize that bevelled cut 50 may be incorporated into first stent section 45 during or after the production of first stent section 45. Specifically, it is possible to produce first stent section 45 having a pre-selected porous design which includes bevelled cut 50 via a computer programmable, high precision laser etching technique. Alternatively, it is possible to use another etching technique to produce first stent section 45 without bevelled cut 50 and thereafter use a precision jig or other means to cut first stent section 45 to produce bevelled cut 50.

Similarly, a second stent section 55 is provided and includes radial cuts 56,57 and a longitudinal cut 58. Radial cuts 56,57 and longitudinal cuts 58 may be produced in second stent section 55 in the manner discussed in the previous paragraph with respect to the production of bevelled cut 50 in first stent section 45. Thereafter, a flap portion 51 of first stent section 45 is folded away from bevelled cut 50. Similarly, a pair of flap 52,53 are folded away from longitudinal cut 58 to expose an opening 54.

First stent section 45 is then lowered to cover opening 54 of second stent section 55. Flaps 52,53 are folded to overlap a portion of first stent section 45. Flap 51 is folded to overlap a portion of second stent section 55. With reference to FIG. 4, it is particularly preferred to adapt the geometry of flaps 52,53 of second stent section 55 such that various of the struts disposed in flaps 52,53 overlap with or are juxtaposed (in plan view) along at least a portion of the length thereof with the struts on first stent section 45 (this is illustrated in more detail hereinbelow with reference to FIG. 16). Preferably, the degree of such overlap or juxtaposition is sufficient to:

(i) facilitate affixing the flaps 52,53 of second stent section 55 to first stent section 45;

(ii) achieve uniform expansion of the stent junction without occurrence of substantial distortion; and (iii) avoid the occurrence of "stent trap" or "stent jail" (usually the result of cracking, buckling or other distortion at the junction of a deployed bifurcated stent making difficult or impossible to deliver a further stent through the stent).

At this point, the flaps may be secured to the respective stent sections by any suitable means such as spot welding (e.g. by a laser or other suitable means), loops, clips and the like. The preferred method of affixing the flaps to the respective stent section is to spot weld them.

A particular advantage of the process illustrated in FIGS. 2–4 is that intersection point 40 (FIG. 1—overlapping flaps not illustrated for clarity) of the resulting stent is reinforced by virtue of disposition of the flaps overlapping a portion of the respective stent sections.

As will be apparent to those of skill in the art, in certain circumstances, it may be possible and even desirable to reduce the size of or even eliminate flap 51. Further, in certain circumstances, it may be possible or even desirable to trim one or both of flaps 52,53 prior to connection of first stent section 45 to second stent section 55.

Figure 5:
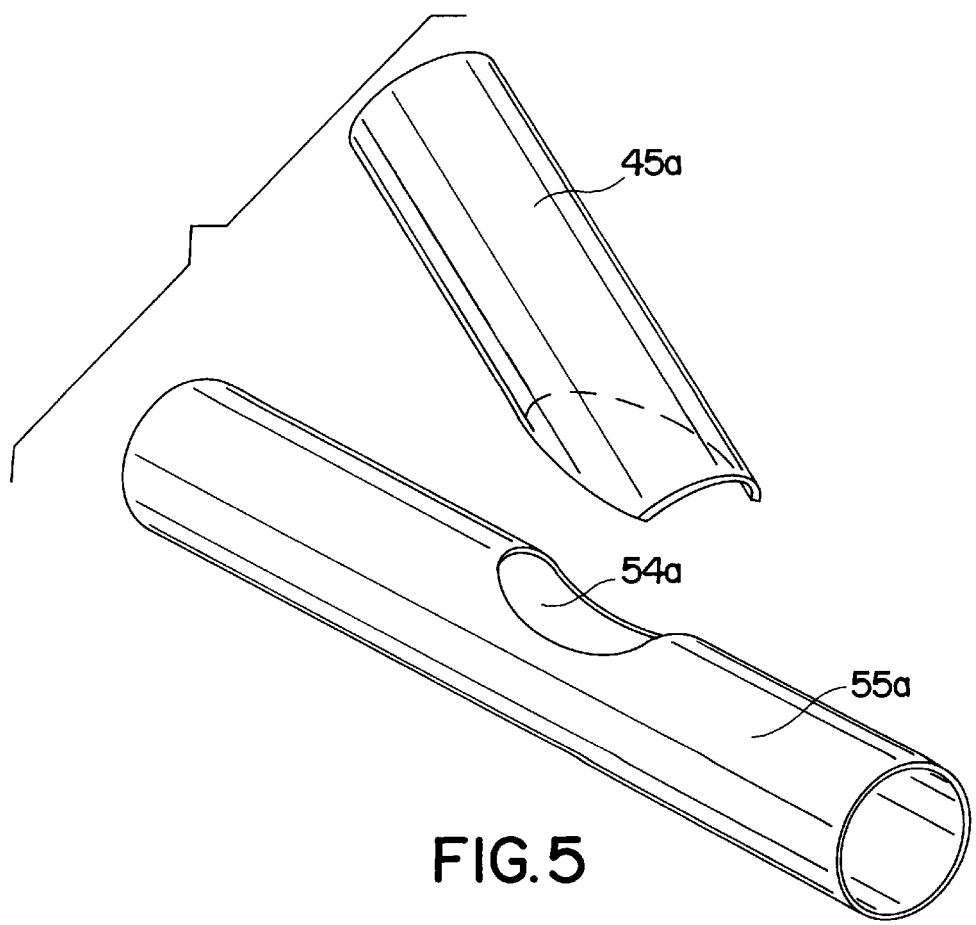
FIG. 5 illustrates a second embodiment of a method for production of a bifurcated stent.

With reference to FIG. 5, there is illustrated another embodiment of the present method for manufacture of a bifurcated stent. In this embodiment, flap 51 (FIGS. 2 and 3) is simply cut away from first stent section 45a. Further, an oval opening 54a is cut into second stent section 55a (i.e. there are no flaps affixed to second stent section 55a). Stent section 45a is then lowered on and connected to second stent section 55a. First stent section 45a and second stent section 55a may be connected to another in the manner described hereinabove with reference to FIG. 2–4.

Figure 6A:
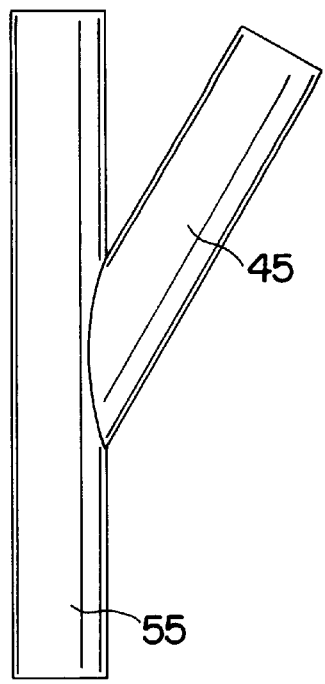
FIGS. 6a and 6b illustrate a post-treatment of a bifurcated stent which has been produced according to the methods illustrated in FIGS. 2–5.
Figure 6B:
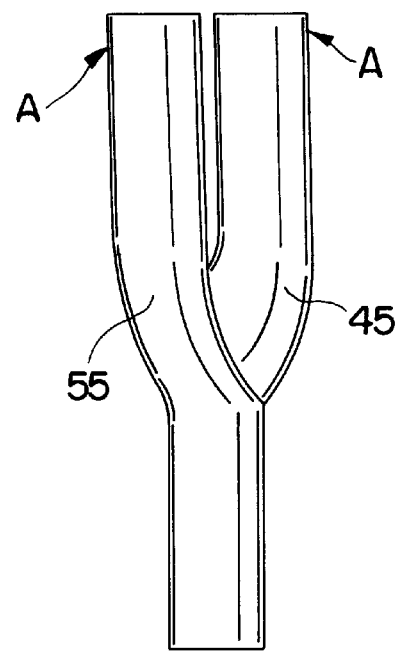

With reference to FIG. 6a, there is illustrated the stent produced by the methods illustrated in FIGS. 2–5. During production of the stent, it is desirable to minimize the angle between first stent section 45 and second stent section 55. Even with this effort, it is preferred that the adjacent termini of first stent section 45 and section stent section 55 are subjected to application of gentle squeezing or other sufficient force in the direction of arrows A to facilitate catheterization of the stent. The result of such post-production treatment of the stent is illustrated in FIG. 6b.

Figure 7:
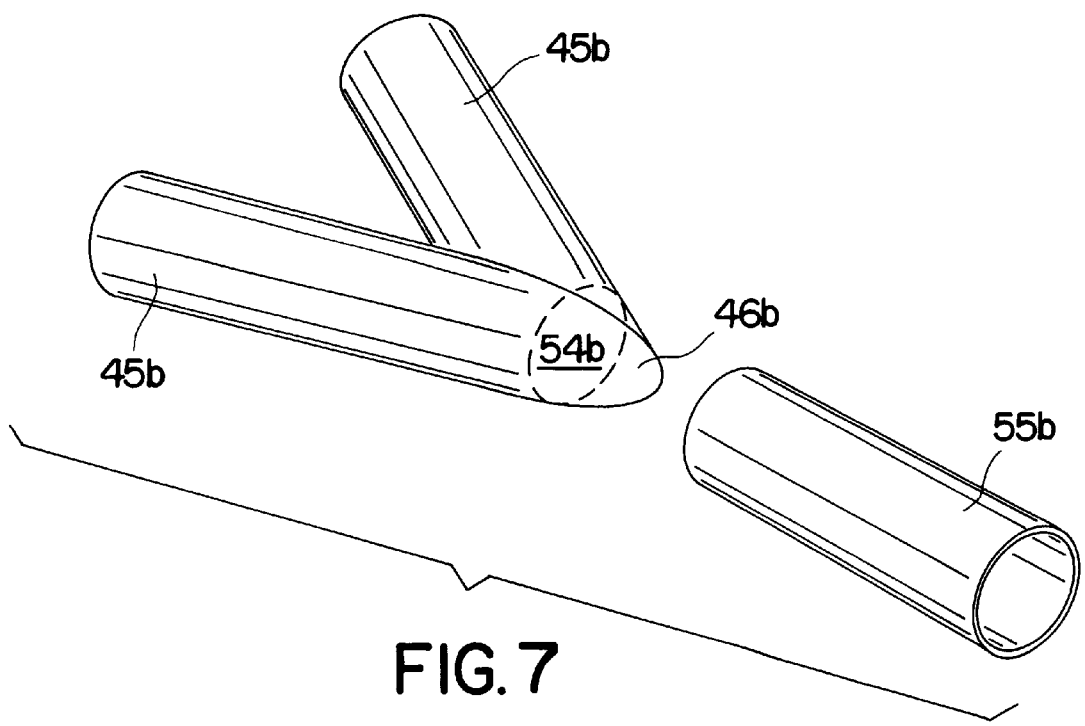
FIGS. 7 and 8 illustrate a third embodiment of a method for production of a bifurcated stent.
Figure 8:
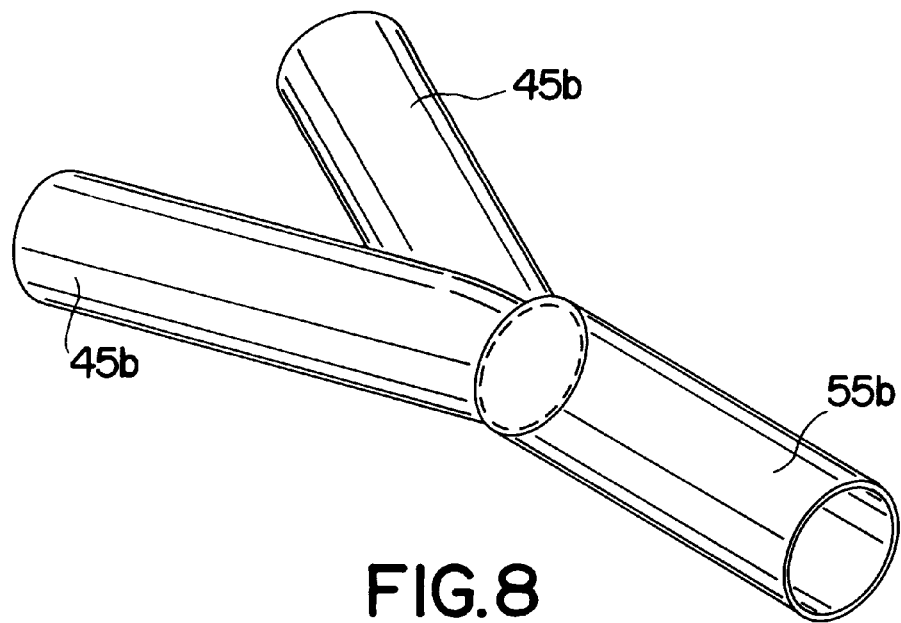

With reference to FIGS. 7 and 8, there is illustrated yet another embodiment of the present method for manufacture of a bifurcated stent. In this embodiment, a pair of first stent sections 45b are secured or affixed to one another. Thereafter, an apex portion 46b of the resulting construction is removed exposing an opening 54b. A second stent section 55b is then connected to opening 54b provided by the combination of first stent sections 45b. The manner of securing second stent section 55b to the periphery of opening 54b created by first stent sections 45b is not particularly restricted and may be effected as discussed hereinabove. As will be appreciated by those of skill in the art, it is possible and, in certain circumstances, desirable, to have one or more flaps on one or move of first stent sections 45b and second stent section 55b. Such flaps would be used in the manner discussed hereinabove in respect of FIGS. 2–4 to overlap a portion of the opposite stent section.

Figure 9:
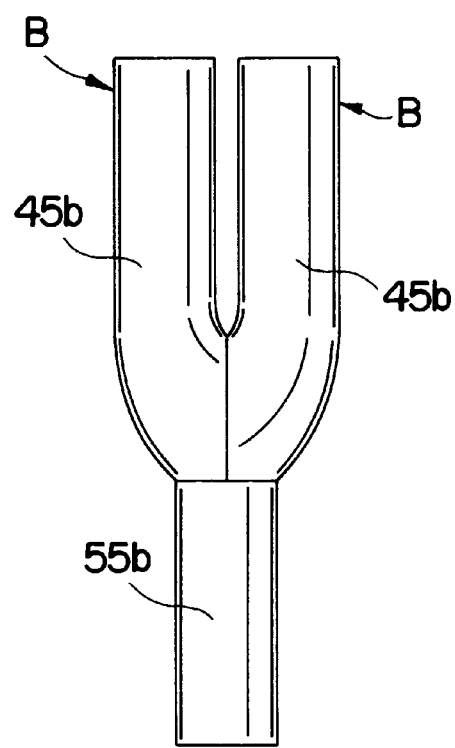
FIG. 9 illustrates a post-treated bifurcated stent which has been produced according to the method illustrated in FIGS. 7 and 8.

With reference to FIG. 9, there is illustrated the stent produced according to the method illustrated in FIGS. 7 and 8 after post-treatment in the manner discussed above in respect of FIGS. 6a and 6b. That is, first stent sections 45b are subjected to application of gentle squeezing or other sufficient force in the direction of arrows B to facilitate catheterization of the stent.

Figure 10:
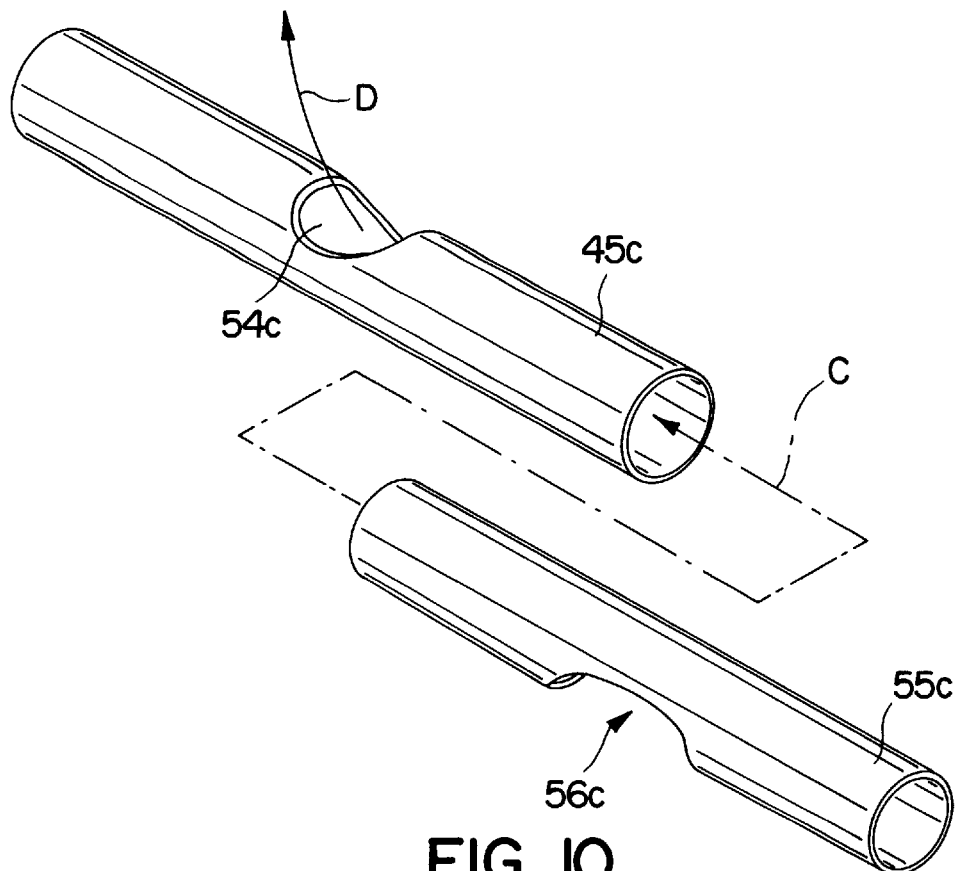
FIGS. 10 and 11 illustrate a fourth embodiment of a method for production of a bifurcated stent.
Figure 11:
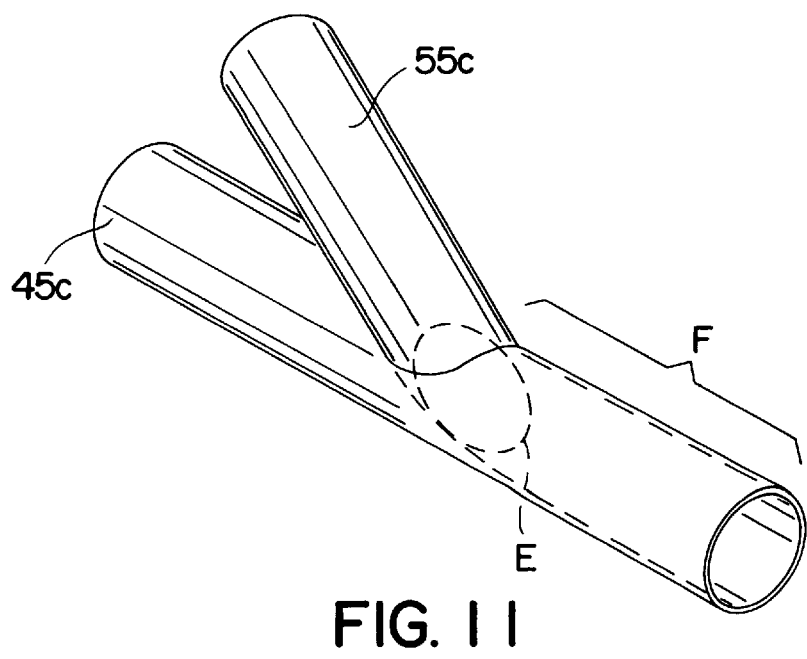

With reference to FIGS. 10 and 11, there is illustrated yet another embodiment of the present method for manufacture of a bifurcated stent. In this embodiment, a first stent section 45c is provided with an opening 54c. A second stent section 55c is provided with an opening 56c. Second stent section 55c has a diameter slightly less than that of first stent section 45c. The difference in diameter between first stent section 45c and second stent section 55c is sufficient to enable coaxial movement of the stent sections with respect to one another with causing damage to either stent section.

As illustrated by arrow C in FIG. 10, the end of second stent section 55c is coaxially fed into an end of first stent section 45c. Once the leading end of second stent section 55c reaches opening 54c of first stent section 45c, it is pulled through opening 54c as illustrated by arrow D in FIG. 10. Second stent section 55c is pulled through opening 54c until opening 56c is aligned with opening 54c—this is illustrated by dashed oval E in FIG. 11.

When practising the method illustrated in FIGS. 10 and 11, care should be taken to design openings 54c and 56c so that they are in alignment when the trailing end of second stent section 55c is flush with the trailing end of first stent section 45c. Further, region F (FIG. 11) of the resulting bifurcated stent is "double reinforced" since it contains a coaxial disposition of first stent section 45c and second stent section 55c. Accordingly, it is possible and, in some cases even desirable, to modify the design of the respective stent sections in this region so that the overall expansion and relative flexibility/rigidity of the stent in this region is commensurate with that of the remaining portion of the stent (i.e. the secondary passageways which branch off from region F in FIG. 11).

While the embodiment illustrated in FIGS. 10 and 11 illustrates the resultant bifurcated stent having a coaxial, overlapping arrangement of stent sections flush at one end, it will be appreciated by those of skill in the art that the length of first stent section 45c or second stent section 55c may be shortened thereby minimizing the size of region F in FIG. 11.

With reference to FIGS. 12–14, there is illustrated a bifurcated body passageway 150 comprised of a proximal passageway 155 and a pair of distal passageways 160,165. As illustrated, bifurcated body passageway 150 comprises a Type "D" Bifurcation lesion having characteristic blockages 170,175,180.

Stent 10 is delivered to bifurcated body passageway 150 in the following manner. Initially, a pair of guidewires 185,190 are inserted into proximal passageway 155 such that guidewire 185 enters distal passageway 160 and guidewire 190 enters distal passageway 165. The manner by which the guidewires are inserted is conventional and within the purview of a person skilled in the art.

As illustrated, stent 10 is positioned in association with a pair of catheters 195,200 (for clarity, the interior of stent 10 is not shown). Catheter 195 has associated with it a balloon 205. Catheter 200 has associated with it a balloon 210. Balloons 205,210 substantially fill primary passageway 25 of stent 10. Balloon 205 substantially fills secondary passageway 30 of stent 10. Balloon 210 substantially fills secondary passageway 35 of stent 10.

The stent/catheter/balloon combination is delivered through proximal passageway 155 with the aid of guidewires 185,190. As the stent/catheter/balloon combination approaches distal passageways 160,165, predisposition of guidewires 185,190 serves to separate secondary passageways 30,35 to be disposed in distal passageways 160,165, respectively. Thus, as illustrated in FIG. 13, stent 10 is positioned in place.

Once stent 10 is in position, balloons 205,210 are expanded resulting in implantation of stent 10 in the corresponding interior surfaces of proximal passageway 155 and distal passageways 160,165. Upon implantation of stent 10, balloons 205,210 are collapsed. Thereafter, catheters 195, 200 and guidewires 185,190 have been removed leaving the implanted stent 10 shown in FIG. 14. As illustrated in FIG. 14, blockages 170,175,180 are bulged radially outwardly in combination with the appropriate portions of proximal passageway 155 and distal passageways 160,165 resulting in a reduction in the overall blockage in bifurcated body passage 150.

It will be apparent to those of skill in the art that implantation of stent 10 can be accomplished by various other means. For example, it is contemplated that it is possible to substitute the pair of catheter/balloon combinations illustrated in FIGS. 12 and 13 with a single, bifurcated catheter/balloon design which mimics the design of the stent. Thus, in this modification, the balloon and guidewire would be design to mimic the bifurcated design of the stent. As further alternative, it is contemplated that the stent can be made of a suitable material which will expand when bifurcated body passageway 150 is flushed with a liquid having an elevated temperature (e.g. 150° F.–160° F.). Further, stent 10 can be designed to expand upon the application of mechanical forces other than those applied by a balloon/catheter. Still further, stent 10 can be designed self-expanding (e.g. by constructing stent from material such as nitinol and the like) to be implanted as described above. In this embodiment, the radially outward force exerted on the stent would be generated within the stent itself.

With reference to FIGS. 15–22, there is illustrated another preferred bifurcated stent in accordance with the present invention. As will be apparent to those of skill in the art, the stent illustrated in FIGS. 15–22 shares many of the features of stent 10 illustrated in FIG. 1.

Figure 16:
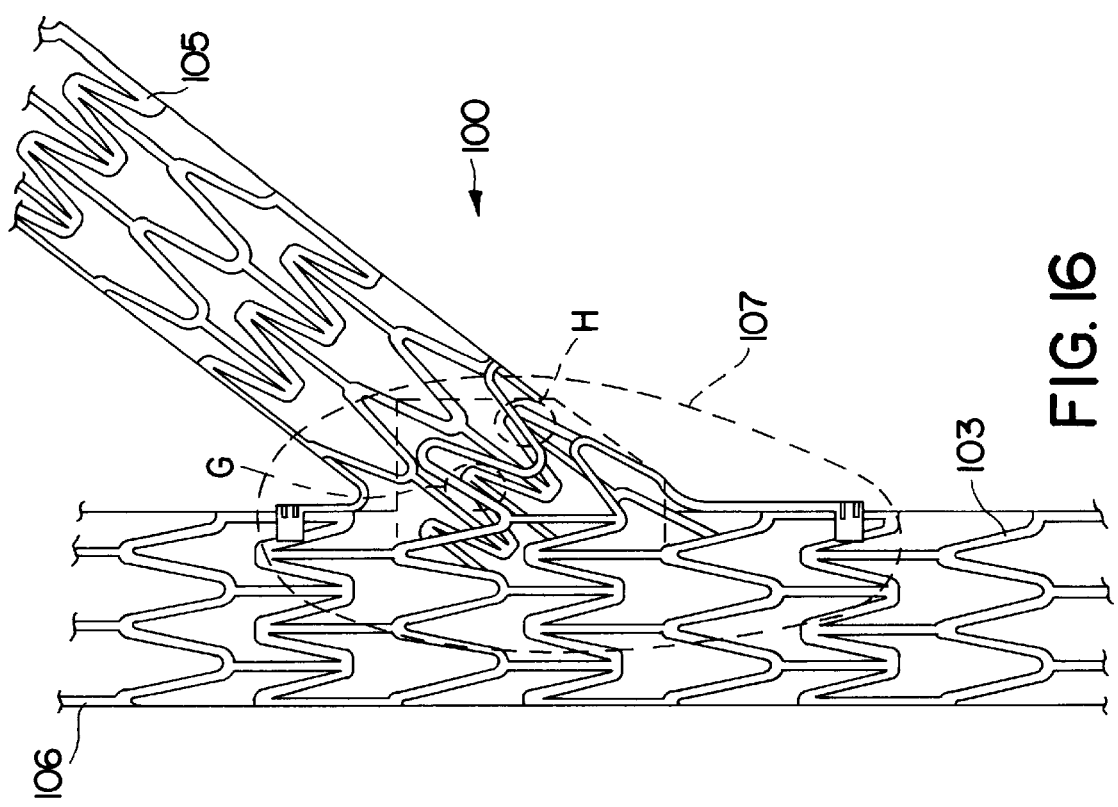
FIGS. 15 and 16 illustrate a side elevation of another bifurcated stent in accordance with the present invention.
Figure 15:
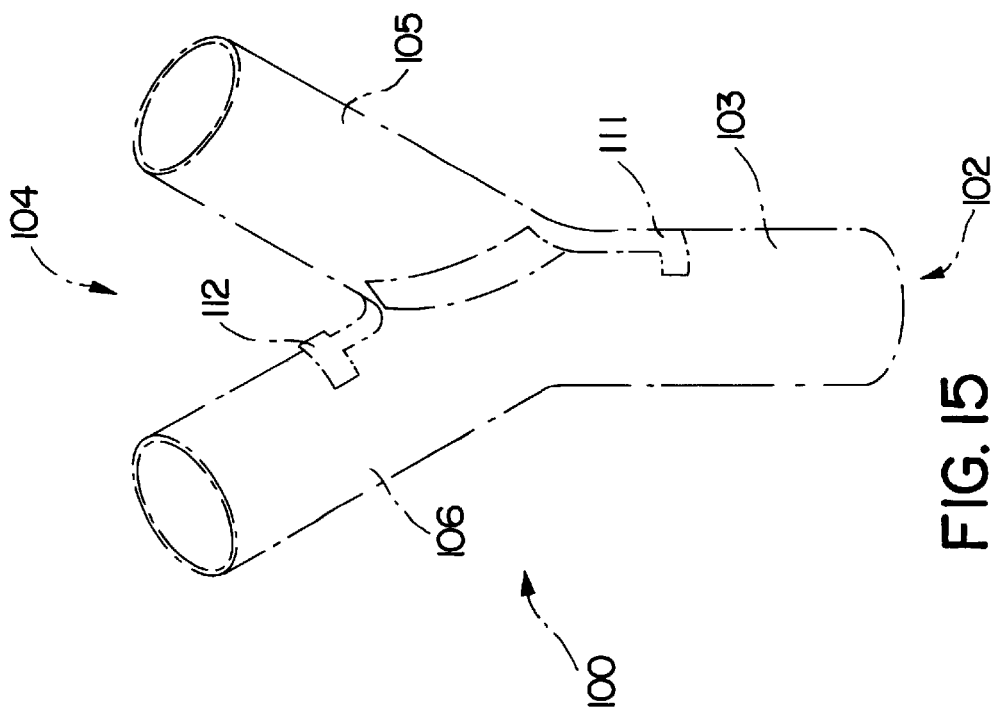

Thus, with reference to FIGS. 15 and 16, there is illustrated a stent 100. FIG. 15 is a side elevation of stent 100 without the porous surface illustrated (for clarity). FIG. 16 is a side elevation of an enlarged portion of stent 100 with the porous surface illustrated. Stent 100 comprises a proximal end 102 and a distal end 104. Proximal end 102 comprises a primary passageway 103. Distal end 104 comprises a pair of secondary passageways 105,106. Secondary passageways 105,106 are connected to primary passageway 103 at an intersection point 107—the nature of intersection point 107 will be further discussed hereinbelow. It is intersection point 107 which distinguishes stent 100 in FIG. 16 from stent 10 in FIG. 1.

As will be apparent to those of skill in the art, stent 100 incorporates the porous surface design illustrated in copending Canadian patent application number 2,134,944, referred to above. As discussed above, this design may be varied to incorporate other designs such as those disclosed in the other Divysio patent applications.

With reference to FIGS. 17–19, manufacture of stent 100 will be discussed. Generally, the manufacture of stent 100 is similar to the manufacture of stent 10 illustrated in FIGS. 1–4 and discussed hereinabove. The principle difference in the manufacture of stent 100 is the use of a modified first stent section 108.

First stent section 108 is constructed from a substantially cylindrical tube 109. A porous surface 110 is disposed on a major portion of cylindrical tube 109. A first connection tab 111 and a second connection tab 112 are also disposed on cylindrical tube 109. As discussed hereinabove, it is possible to produce first section 108 comprising porous 110, first connection tab 111 and second connection tab 112 using computer programmable, high precision laser etching techniques or by other etching techniques in combination with precision jig techniques. This results in an end of porous surface 110 comprising first connection tab 111, second connection tab 112 and a bevelled edge 113. The product of the cutting techniques is illustrated in FIG. 18.

FIG. 19 is an enlarged perspective view of a portion of first connection tab 111 (second connection tab 112 is preferably the same). As illustrated, first connection tab 111 comprises a stem 114 and a head 115. Preferably, stem 114 and/or head 115 are curved to have a shape complementary to the outer surface of the second section to which first stent section 108 is connected (discussed in more detailed hereinbelow). Stem 114 and head 115 comprise a plurality of slots 116 disposed therein. Slots 116 may be disposed in stem 114 and head 115 by the use of a computer programmable, high precision laser as described above. Preferably, slots 116 are disposed throughout the thickness of stem 114 and head 115. Slots 116 may be may have a straight or tapered cross-section. Preferably, slots 116 have a thickness in the range of from about 0.0015 to about 0.004 inches. Head 115 further comprises solid (i.e., slot-free or non-porous) regions 117.

Thus, in the embodiment illustrated in FIG. 19, slots 116 serve to from a porous surface in first connection tab 111 (second connection tab 112 is preferably the same). While it is preferred to have such a porous surface disposed in the connection tabs, the precise nature of the porosity is not particularly restricted. The provision of a porous surface, particularly at head 115, facilitates expansion of the connection tab while minimizing or avoiding the occurrence of cracking or distortion.

After the production of first stent section 108, first connection tab 111 and second connection tab 112 are bent or otherwise moved to be substantially collinear with the periphery of bevelled edge 113 (i.e., as illustrated in FIG. 118). At this point, first stent section 108 may be connected to another stent section of a design similar to second stent section 55 discussed hereinabove with reference to FIGS. 2–4—see intersection point 107 in FIG. 16. In this embodiment, as in the embodiments illustrated in FIGS. 2–4, it is preferred to adapt the geometry of flaps 52,53 of second stent section 55 such that various of the struts disposed in flaps 52,53 overlap along at a portion of the length thereof with the struts on first stent section 108. See, for example, regions G and H in FIG. 16 which illustrates an embodiment of such partial overlap and juxtaposition (in plan view). Of First connection tab 111 and second connection tab 112 may be secured to the second stent section as described above. Specifically, it is particularly preferred to connect solid (i.e., non-porous) regions to the section stent portion.

Figure 20:
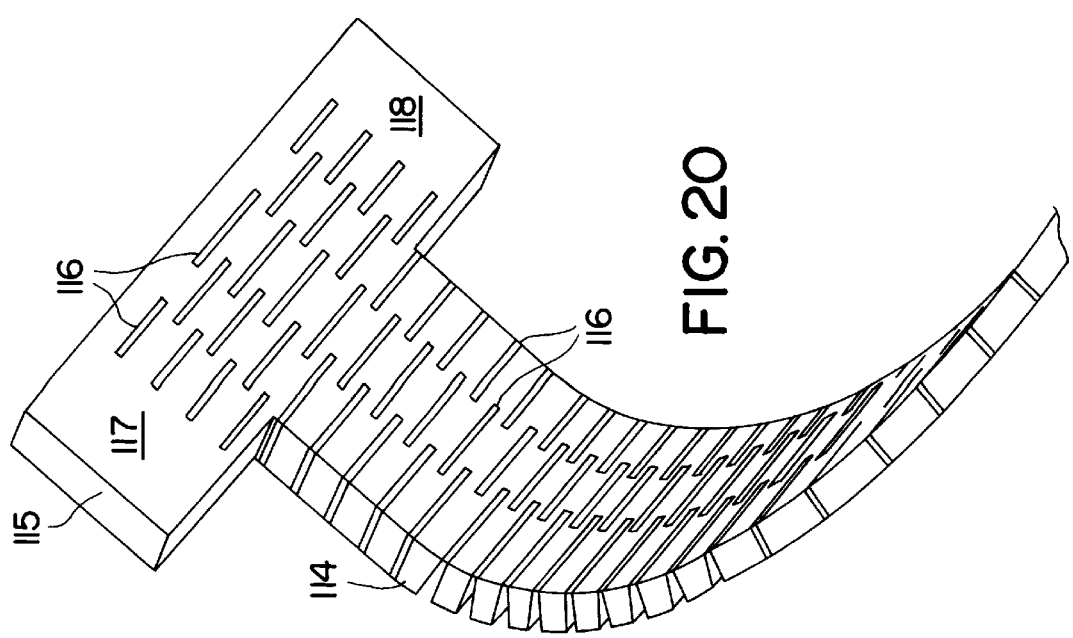

The benefits accruing from the use of first stent section 108 in the production a bifurcated stent include:

1. The provision of at least one solid (i.e., non-porous) region in the connection tabs facilitates attachment of the respect stent sections to one another (e.g. laser welding is facilitated significantly);
2. The provision of a porous surface in at least a portion of the connection tabs facilitates bending thereof for connection of the respective stent sections; and
3. The provision of slots 116, particularly in second connection tab 112 (see FIG. 15), allows the slots to function as a solid state valve at the "crotch" of the bifurcated stent thereby providing sealed, reinforcement of the bifurcated stent in this crucial region—this is illustrated in FIG. 20 which depicts tapered openings for slots 116 and the apex of the bend in stem 114.

Figure 21:
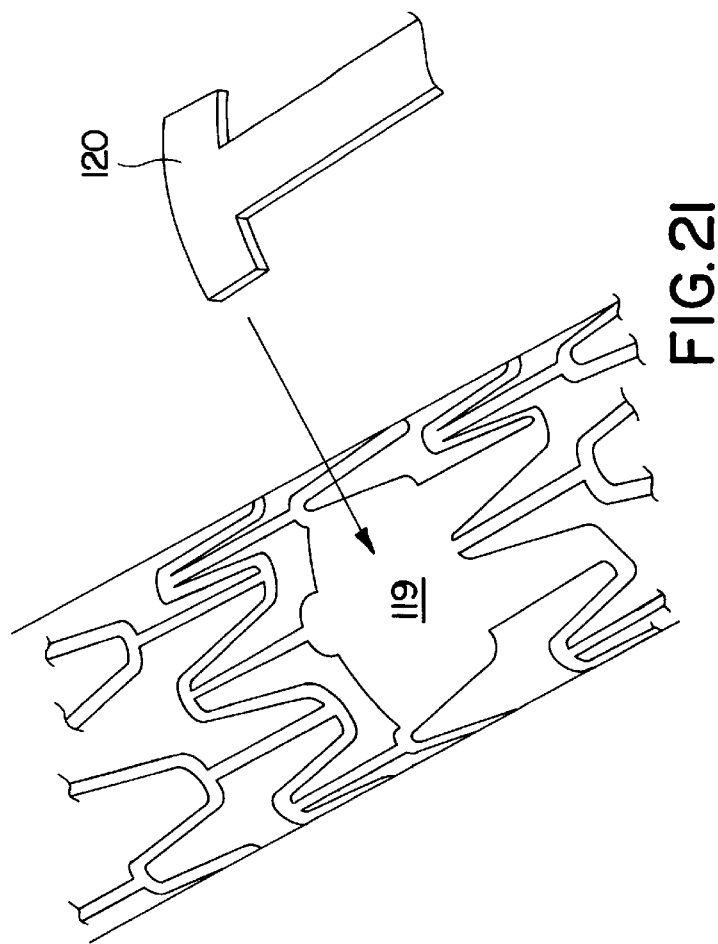

FIG. 21 illustrates an alternate embodiment of the embodiment illustrated in FIGS. 15–20. Specifically, in FIG. 21, second stent section 55, otherwise the same as that described hereinabove with reference to FIGS. 1–4, is adapted to include a landing 119 for receiving a solid (i.e. non-slot or non-porous) connection tab 120. Landing 119 may be connected to connection tab 120 as described hereinabove.

Figure 22:
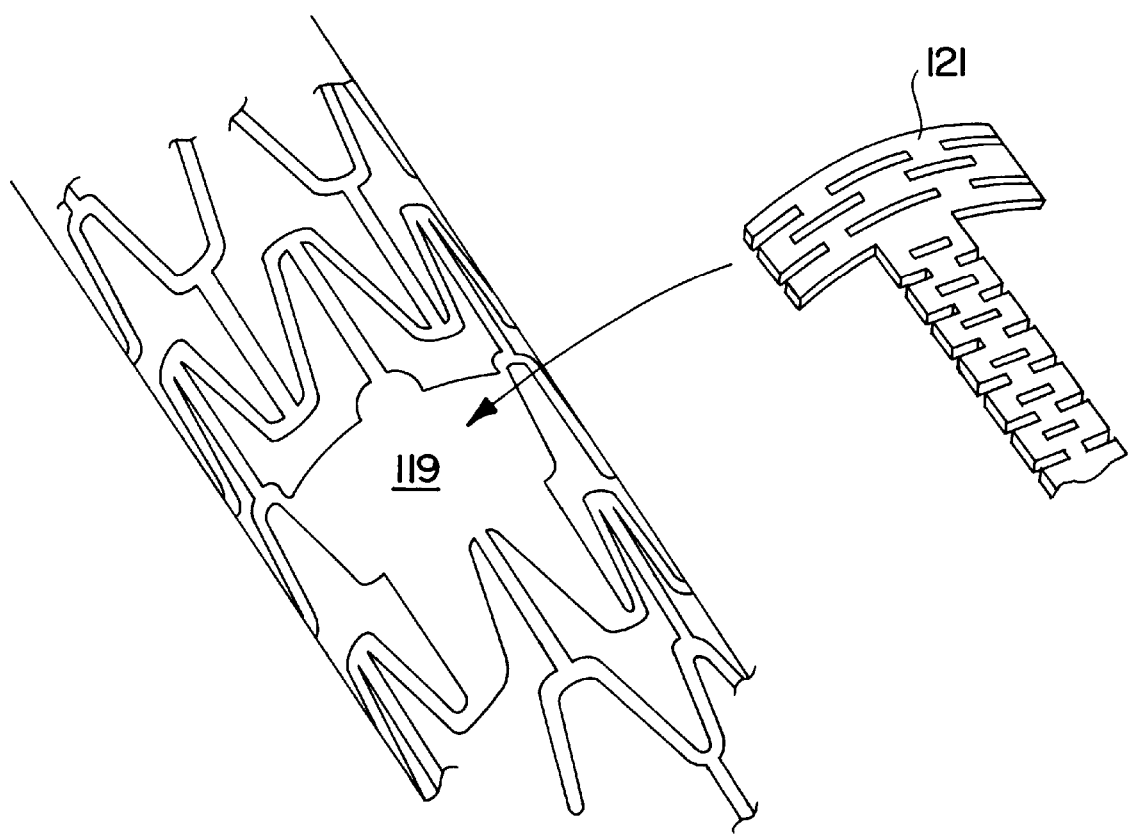

With reference to FIG. 22, there is illustrated a variant to the embodiment illustrated in FIG. 21. Specifically, in FIG. 22, a connection tab 121 having the entire surface thereof slotted and otherwise porous is connected to landing 119.

While this invention has been described with reference to illustrative embodiments, this description is not intended to be construed in a limiting sense. Various modifications of the illustrative embodiments, as well as other embodiments of the invention, will be apparent to persons skilled in the art upon reference to this description. For example, while first connection tab 111 and second connection tab 112 have been illustrated as being attached to first stent portion 108, it is possible to have these tabs integral with second stent portion 55. Alternatively, the connection tabs do not have to integral with either of the stent portions and, instead, can be custom-designed, independent connection tabs which are affixed to both stent portions. Still further, it is possible for the connection tabs (integral or independent) to have a different thickness than either of the stent sections. It is therefore contemplated that the appended claims will cover any such modifications or embodiments.

What is claimed is:

1. An ex vivo expandable bifurcated stent comprising a proximal end and a distal end in communication with one another, the proximal end comprising a primary passageway and the distal end comprising a pair of secondary passageways, each secondary passageway coupled to the primary passageway at a first intersection, the stent being expandable from a first, contracted position to a second, expanded position upon the application of a radially outward force exerted on the stent, each of the primary passageway and the second passageways being constructed of a tubular wall having a porous surface, at least one reinforcing member being disposed at the first intersection for reinforcing the first intersection, said reinforcing member overlapping at least one of (i) said primary passageway, (ii) a first of said secondary passageways, and (iii) a second of said secondary passageways, said reinforcing member being separate structure from same first intersection.

2. The bifurcated stent defined in claim 1, wherein the stent comprises a first stent section connected to a second stent section.

3. The bifurcated stent defined in claim 2, wherein an end of the first stent section is connected to an opening disposed along a length of the second stent section.

4. The bifurcated stent defined in claim 3, wherein a first connection portion is disposed at an end of the first stent section and is connected to the second stent section.

5. The bifurcated stent defined in claim 4, wherein the first connection portion is integral with an end of the first stent section.

6. The bifurcated stent defined in claim 4, wherein the first connection portion comprises a porous section and a non-porous section, the non-porous section connected to the second stent section.

7. The bifurcated stent defined in claim 6, wherein the porous section comprises a plurality of elongate slots.

8. The bifurcated stent defined in claim 7, wherein the elongate slots traverse the thickness of at least one connection tab.

9. The bifurcated stent defined in claim 7, wherein the elongate slots are disposed substantially orthogonal to a longitudinal axis of the first stent section.

10. The bifurcated stent defined in claim 2, wherein the second stent section comprises a second connection portion along at least a portion of the periphery of the opening, the second connection portion connected to the first stent section.

11. The bifurcated stent defined in claim 2, wherein the first stent section and the second stent section are coaxially disposed with respect to one another along at least a portion of the primary passageway.

12. The bifurcated stent defined in claim 2, wherein the first stent section and the second stent section are coaxially disposed with respect to one another along substantially the entire length of the primary passageway.

13. The bifurcated stent defined in claim 2, wherein the first stent section and the second stent section are connected to one another and to a third stent section, at least one of the stent sections comprising the primary passageway and each of the other to stent sections comprising a secondary passageway.

14. The bifurcated stent defined in claim 1, wherein the at least one connection portion interconnects the pair of secondary passageways.

15. The bifurcated stent defined in claim 1, wherein the at least one connection portion connects one of the pair of second passageways to the primary passageway.

16. A stent according to claim 1, wherein the reinforcing member is integral with the first of said secondary passageways and is coupled to the second of said secondary passageways.

17. A stent according to claim 1, wherein the reinforcing member is integral with the first of said secondary passageways and overlaps said primary passageway.

18. A stent according to claim 1, wherein said first secondary passageway and said second secondary passageway form a crotch, and wherein said reinforcing member is disposed in said crotch.

19. A stent according to claim 1, wherein said reinforcing member extends circumferentially less than the entire circumference of the passageway which it overlaps.

20. A stent according to claim 1, wherein an open-faced end of one of said secondary passageways is coupled to a corresponding opening in said primary passageway.

21. A stent according to claim 1, wherein said reinforcing member comprises a T-shaped tab wherein the top portion of said tab extends circumferentially around a portion of the overlapped passageway.

22. A stent according to claim 1, wherein said reinforcing member extends from the second of said secondary passageways and overlaps said primary passageway, and further comprising a further reinforcing member which extends from said second secondary passageway and overlaps said first secondary passageway.

23. A method for production of an ex vivo bifurcated stent comprising the steps of:
   connecting a first stent section to a second stent section at an intersection, the first stent section having an end thereof adapted for connection to an opening disposed along the length of a second stent section, each of said first stent section and said second stent section being constructed of a tubular wall having a porous surface; and
   disposing a reinforcing member at an intersection between said first stent section and said second stent section, said reinforcing member overlapping at least one of (i) said first stent section, and (ii) said second stent section, said reinforcing member being separate structure from the intersection between said first stent section and said second stent section.

24. The method defined in claim 23, wherein the end of the first stent section adapted for connection is bevelled with respect to a longitudinal axis of the first stent section.

25. The method defined in claim 23, comprising the further step of disposing at least one second flap portion at a periphery of the opening disposed along the length of the second stent section.

26. The method defined in claim 23, comprising the further step of disposing a pair of second flap portions at a periphery of the opening disposed along the length of the second stent section.

27. The method defined in claim 26, wherein, prior to the connecting step, at least one second flap portion is trimmed to a reduced size.

28. The method defined in claim 26, comprising the further step of overlapping the at least one second flap portion of the second stent section on to a portion of the first stent section.

29. The method defined in claim 28, wherein the connecting step comprises welding the at least one second flap portion of the second stent section to the first stent section.

30. The method defined in claim 26, wherein, prior to the connecting step, at least one second flap portion is removed.

31. The method defined in claim 23, comprising the further steps of producing the second stent section by:
   providing a pair of third stent sections, each third stent sections having an end thereof bevelled with respect to a longitudinal axis of the third stent section;
   joining the pair of third stent sections in a complementary manner at each bevelled end thereof to provide a substantially V-shaped stent section; and
   removing an apex portion of the V-shaped stent section to define the second stent section having an opening therein.

32. The method defined in claim 31, wherein the connecting step comprises connecting the end of the first stent section to the opening defined in the V-shaped stent section.

33. The method defined in claim 23, wherein the connecting step comprises welding the first stent section to the second stent section.

34. A method for production of a bifurcated stent comprising the steps of:
   connecting a first stent section to a second stent section, the first stent section having an end thereof adapted for connection to an opening disposed along the length of a second stent section; and
   disposing at least one first flap portion at the end of the first stent section adapted for connection to a portion of the second stent section.

35. The method defined in claim 34, wherein the at least one flap portion comprises a connection tab having a non-porous surface disposed on at least a portion thereof.

36. The method defined in claim 34, wherein the at least one flap portion comprises a connection tab having a porous surface disposed on at least a portion thereof.

37. The method defined in claim 36, wherein the porous surface comprises a plurality of substantially elongate slots.

38. The method defined in claim 34, wherein the at least one flap portion comprises a connection tab having both a porous surface and non-porous surface disposed thereon.

39. The method defined in claim 38, wherein the porous surface comprises a plurality of substantially elongate slots.

40. The method defined in claim 34, wherein the at least one first flap portion is produced by folding from the end of the first stent section adjacent the bevelled cut.

41. The method defined in claim 34, wherein, prior to the connecting step, the at least one first flap portion is trimmed to a reduced size.

42. The method defined in claim 34, comprising the further step of overlapping the at least one first flap portion of the first stent section on to a portion of the second stent section.

43. The method defined in claim 42, wherein the connecting step comprises welding the at least one first flap portion of the first stent section to the second stent section.

44. The method defined in claim 34, wherein, prior to the connecting step, the at least one first flap portion is removed.

45. A method for production of a bifurcated ex vivo stent comprising the steps of:

passing a first stent section having a first opening disposed along a length thereof through a second stent section having a second opening disposed along a length thereof, the first stent section having a diameter less than a diameter of the second stent section, the first stent section and the second stent section each comprising a tubular wall having a porous surface;

passing a leading end of the first stent section through the second opening of the second stent section;

substantially aligning the first opening and the second opening with respect to one another at an intersection; and affixing the first stent section to the second stent section with a reinforcing member that overlaps at least one of the first stent section and the second stent section, the reinforcing member being a separate structure from the intersection between the first stent section and the second stent section.

46. An expandable ex vivo bifurcated stent comprising a proximal end and a distal end in communication with one another, the proximal end comprising a primary passageway and the distal end comprising a pair of secondary passageways, each secondary passageway in communication with the primary passageway at a first intersection, the stent being expandable from a first, contracted position to a second, expanded position upon the application of a radially outward force exerted on the stent, each of the primary passageway and the secondary passageways having a porous surface, each of said primary passageway and said secondary passageway comprising a tubular wall, at least one reinforcing portion interconnecting the pair of secondary passageways for reinforcing the first intersection, said reinforcing portion overlapping at least one of the secondary passageways, said reinforcing portion being separate structure from the first intersection between the primary passageway and the secondary passageways.

\* \* \* \* \*